(12) United States Patent
Yoshimoto et al.

(10) Patent No.: US 9,765,179 B2
(45) Date of Patent: Sep. 19, 2017

(54) METHOD FOR PRODUCING BIPHENYL-SKELETON-CONTAINING EPOXY RESIN

(71) Applicant: DIC Corporation, Tokyo (JP)

(72) Inventors: Yasuyo Yoshimoto, Sakura (JP);
Kunihiro Morinaga, Sakura (JP);
Hiroshi Kinoshita, Sakura (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/890,237

(22) PCT Filed: May 15, 2014

(86) PCT No.: PCT/JP2014/062936
§ 371 (c)(1),
(2) Date: Nov. 10, 2015

(87) PCT Pub. No.: WO2014/185485
PCT Pub. Date: Nov. 20, 2014

(65) Prior Publication Data
US 2016/0083504 A1    Mar. 24, 2016

(30) Foreign Application Priority Data

May 15, 2013    (JP) .................................. 2013-103011

(51) Int. Cl.
*C08G 59/00* (2006.01)
*C08G 65/08* (2006.01)
(Continued)

(52) U.S. Cl.
CPC ......... *C08G 59/063* (2013.01); *C07D 303/30* (2013.01); *C07D 405/10* (2013.01); *C07D 405/14* (2013.01); *C08G 59/02* (2013.01)

(58) Field of Classification Search
CPC .. C07D 303/30; C07D 405/14; C07D 405/10; C08G 59/063; C08G 59/02
(Continued)

(56) References Cited

U.S. PATENT DOCUMENTS 3,374,203 A    3/1968    Schmukler
3,721,644 A    3/1973    Stoffey
(Continued)

FOREIGN PATENT DOCUMENTS

JP    02-209971 A    8/1990
JP    06-264301 A    9/1994
(Continued)

OTHER PUBLICATIONS

Office Action dated Jun. 30, 2015, issued for the Japanese patent application No. 2015-513932.
(Continued)

*Primary Examiner* — David Karst
(74) *Attorney, Agent, or Firm* — Locke Lord LLP (57) ABSTRACT

Disclosed is a method for producing a biphenyl-skeleton-containing epoxy resin represented by Formula (1) described below including a step of allowing polyvalent hydroxy biphenyl obtained by a production step including a regioselective cross-coupling reaction to react with epihalohydrin.

(1)

$$\left(\underset{(R^1)_{n1}}{\overbrace{\bigcirc\diagdown_{O}}}\right)_n \underset{(R^2)_{k1}}{\overbrace{\phantom{xxxxx}}} \left(\underset{O\diagup}{\overbrace{O\diagup}}\right)_m$$

(Continued)

(In the formula, k1 and l1 each represent an integer of 0 to 4, m and n each represent an integer of 1 to 5, $R^1$ and $R^2$ each independently represent a hydrocarbon group having 1 to 10 carbon atoms which may have a substituent group, and $R^1$ and $R^2$ may be identical to each other or different from each other. (Provided that left and right phenyl structures of a biphenyl skeleton are different from each other.)

2 Claims, 2 Drawing Sheets

(51) Int. Cl.

| | |
|---|---|
| *C08G 65/04* | (2006.01) |
| *C08G 59/06* | (2006.01) |
| *C07D 303/30* | (2006.01) |
| *C08G 59/02* | (2006.01) |
| *C07D 405/14* | (2006.01) |
| *C07D 405/10* | (2006.01) |

(58) Field of Classification Search
 USPC .................................................. 528/87, 421
 See application file for complete search history.

(56) References Cited

U.S. PATENT DOCUMENTS

| | | |
|---|---|---|
| 5,162,162 A | 11/1992 | Yasuda et al. |
| 2004/0254327 A1 | 12/2004 | Boyles et al. |

FOREIGN PATENT DOCUMENTS

| | | |
|---|---|---|
| JP | 3476027 B2 | 12/2003 |
| JP | 3947490 B2 | 7/2007 |
| JP | 3989458 B2 | 10/2007 |

OTHER PUBLICATIONS

International Search Report dated Jul. 29, 2014, issued for PCT/JP2014/062936.

MASS TO CHARGE RATIO (m/z)

METHOD FOR PRODUCING BIPHENYL-SKELETON-CONTAINING EPOXY RESIN

TECHNICAL FIELD

The present invention relates to a method for producing a biphenyl-skeleton-containing epoxy resin and an epoxy resin.

BACKGROUND ART

A polyvalent hydroxy compound and an epoxy resin using the polyvalent hydroxy compound have been widely used in a semiconductor encapsulation material or an electronic component such as a print circuit board, electronic component fields, a conductive adhesive agent such as a conductive paste, other adhesive agents, a matrix for a composite material, a coating material, a photoresist material, a developing material, and the like from a viewpoint of providing a cured product having low shrinkage (dimensional stability) at the time of curing, and excellent electrical insulation and chemical resistance. Recently, in such various applications, particularly, in advanced material fields, performance represented as heat resistance or moisture absorption resistance, and low thermal expandability has been required to be further improved. Further, according to the laws and regulations with respect to environmental problems, solder having a high melting point which does not use lead (lead free solder) has been mainly used, and the lead free solder has a working temperature approximately 20° C. to 40° C. higher than that of eutectic solder of the related art, and thus heat resistance which is higher than ever before has been required in the cured product of the epoxy resin.

An epoxy resin having a biphenyl in a molecular skeleton disclosed in PTL 1 has particularly excellent various physical properties such as high heat resistance, low thermal expandability, and moisture resistance. Further, the epoxy resin has crystalline properties at an ordinary temperature, and thus has low viscosity even in a solid resin just like in a liquid resin at the time of being melted. Accordingly, when the epoxy resin is used in a encapsulation material, excellent fluidity is able to be obtained even at the time of being highly filled with silica, and thus the epoxy resin has excellent workability and excellent performance. However, recently, for heat resistance, higher performance has been required, and thus it is necessary that the heat resistance is further enhanced. In order to improve the heat resistance, an increase in crosslinking density, that is, multifunctionalization is effective, and as disclosed in PTL 2 and PTL 3, an epoxy resin having a phenol compound as a skeleton in which phenols are introduced to a biphenyl skeleton as a repeating structure is multifunctionalized, but the molecular weight increases, and thus an increase in a softening point or a melt viscosity occurs. In addition, the multifunctionalization due to an increase in the molecular weight is insufficient to correspond to the recent demand for high heat resistance. In order to improve the heat resistance while maintaining liquid properties or a low melt viscosity, it is necessary that a multifunctional epoxy resin having a low molecular weight is obtained with high purity.

CITATION LIST

Patent Literature

[PTL 1] Japanese Patent No. 3947490
[PTL 2] Japanese Patent No. 3989458
[PTL 3] Japanese Patent No. 3476027

SUMMARY OF INVENTION

Technical Problem

An object of the present invention is to provide a biphenyl-skeleton-containing epoxy resin of which a cured product expresses excellent heat resistance, low thermal expandability, and high thermal conductivity, and has liquid properties or a low melt viscosity, and a method for producing the biphenyl-skeleton-containing epoxy resin.

Solution to Problem

As a result of intensive studies by the present inventors, it has been found that an epoxy resin in which polyvalent hydroxy biphenyl with high purity obtained by a regioselective cross-coupling reaction of a phenol derivative is glycidylated has liquid properties or a low melt viscosity, and a cured product of the epoxy resin has excellent heat resistance, low thermal expandability, and excellent thermal conductivity, and thus the present invention has been accomplished.

That is, the present invention relates to [1] to [5] described below.

[1]
A method for producing a biphenyl-skeleton-containing epoxy resin represented by Formula (1) described below, including a step of allowing polyvalent hydroxy biphenyl obtained by a production step including a regioselective cross-coupling reaction to react with epihalohydrin.

[Chem. 1]

(In the formula, k1 and l1 each represent an integer of 0 to 4, m and n each represent an integer of 1 to 5, $R^1$ and $R^2$ each independently represent a hydrocarbon group having 1 to 10 carbon atoms which may have a substituent group, and $R^1$ and $R^2$ may be identical to each other or different from each other, provided that left and right phenyl structures of a biphenyl skeleton are different from each other.)

[2]
The method for producing a biphenyl-skeleton-containing epoxy resin according to [1], in which the regioselective cross-coupling reaction is a cross-coupling reaction using at least one compound selected from aryl boronic acids and an anhydride thereof, ester and a borate salt represented by Formula (2) described below, and at least one compound selected from aryl halide or aryl sulfonate represented by Formula (3) described below.

[Chem. 2]

-continued

[Chem. 3]

(3)

(k1 and l1 each represent an integer of 0 to 4, m and n each represent an integer of 1 to 5, $R^1$ and $R^2$ each independently represents a hydrocarbon group having 1 to 10 carbon atoms which may have a substituent group, $R^1$ and $R^2$ may be identical to each other or different from each other, $R^3$ and $R^4$ each independently represent a hydrogen atom, a methyl group, a benzyl group, a tetrahydropyranyl group, a tetrahydrofuryl group, a methoxymethyl group, an ethoxymethyl group, or a silyl group such as a trimethyl silyl group, a tert-butyl dimethyl silyl group, and a triisopropyl silyl group, and X represents a chlorine atom, a bromine atom, an iodine atom, triflate, mesylate, tosylate, or nosylate.)

[3]

A biphenyl-skeleton-containing epoxy resin represented by Formula (1) which is obtained by the method for producing a biphenyl-skeleton-containing epoxy resin according to [1] or [2].

[Chem. 4]

(1)

(In the formula, k1 and l1 each represent an integer of 0 to 4, m and n each represent an integer of 1 to 5, $R^1$ and $R^2$ each independently represent a hydrocarbon group having 1 to 10 carbon atoms which may have a substituent group, and $R^1$ and $R^2$ may be identical to each other or different from each other, provided that left and right phenyl structures of a biphenyl skeleton are different from each other.)

[4]

A 2,4,4'-trihydroxy biphenyl type epoxy resin represented by Formula (4) which is obtained by the method for producing a biphenyl-skeleton-containing epoxy resin according to [1] or [2].

[Chem. 5]

(4)

(In the formula, k1 represents an integer of 0 to 4, l1 represents an integer of 0 to 3, $R^1$ and $R^2$ each independently represent a hydrocarbon group having 1 to 10 carbon atoms which may have a substituent group, and $R^1$ and $R^2$ may be identical to each other or different from each other.)

[5]

A 3,4',5-trihydroxy biphenyl type epoxy resin represented by Formula (5).

[Chem. 6]

(5)

(In the formula, k1 represents an integer of 0 to 4, l1 represents an integer of 0 to 3, $R^1$ and $R^2$ each independently represent a hydrocarbon group having 1 to 10 carbon atoms which may have a substituent group, and $R^1$ and $R^2$ may be identical to each other or different from each other.)

Advantageous Effects of Invention

According to the present invention, it is possible to provide a method for producing a biphenyl-skeleton-containing epoxy resin which has liquid properties or a low melt viscosity and exhibits excellent solvent solubility, and an epoxy resin, and a cured product of the epoxy resin exhibits excellent heat resistance, low linear expandability, excellent moisture resistance, and high thermal conductivity.

DESCRIPTION OF EMBODIMENTS

Hereinafter, the present invention will be described in detail.

According to the present invention, in producing of a biphenyl-skeleton-containing epoxy resin represented by Formula (1) described below in which epihalohydrin reacts with polyvalent hydroxy biphenyl, a regioselective cross-coupling reaction is performed in a production step of polyvalent hydroxy biphenyl having high purity which is a raw material.

[Chem. 7]

(1)

(In the formula, k1 and l1 each represent an integer of 0 to 4, m and n each represent an integer of 1 to 5, $R^1$ and $R^2$ each independently represent a hydrocarbon group having 1 to 10 carbon atoms which may have a substituent group, and $R^1$ and $R^2$ may be identical to each other or different from each other, provided that left and right phenyl structures of a biphenyl skeleton are different from each other.)

In the production of the biphenyl-skeleton-containing epoxy resin of the present invention, the polyvalent hydroxy biphenyl which is the raw material is obtained by a production method including a regioselective cross-coupling reaction. The regioselective cross-coupling reaction is a reaction in which when a biphenyl structure is constructed by forming a C—C bond between carbons on two aromatic rings, the position of two bonded carbons is limited, and the bonding does not occur in the position of other carbons, and polyvalent hydroxy biphenyl having high purity is able to be obtained. That is, the regioselective cross-coupling reaction is a reaction which progresses by substituent group-metal exchange between a substituent group such as halogen existing on the carbon relevant to the bonding in addition to a hydrogen atom and a metal catalyst.

In the coupling reaction constructing the biphenyl skeleton, for example, as in a method disclosed in PTL 1, a reaction is also included in which a phenoxy radical is generated during the reaction and a C—C bond is regioselectively formed, but in order to express regioselectivity, there are many regulations such as a limitation in the position of the hydroxyl group in the stereoscopic structure of the raw material or a demand for introduction of a substituent group for suppressing a side reaction, and there are problems such as difficulty of preventing a multimer or a byproduct from being generated.

In contrast, in the reaction progressing by the substituent group-metal exchange between the substituent group and the metal catalyst, the hydroxyl group may be in a position such as an ortho position, a meta position, and a para position of a reaction point, and thus a range of selecting a structure is wide, a homocoupling product which is a byproduct in the cross-coupling is not generated, and multimerization does not occur. For this reason, the reaction is suitable for producing a precursor of a multifunctional low molecular weight epoxy resin having high purity.

A known and common method is able to be used insofar as the regioselective coupling reaction included in the method for producing the polyvalent hydroxy biphenyl having high purity in the present invention is a reaction using a raw material having a substituent group which is able to be subjected to substituent group-metal exchange with respect to a metal catalyst on carbon relevant to the formation of a C—C bond.

Examples of the regioselective cross-coupling reaction described above include a reaction in which any two of the following aryl compounds are coupled by using the following metal catalyst. Examples of the aryl compound include a halogeno group such as chloro, bromo, and iodo; a silyl group such as trimethyl silyl, trimethoxy silyl, trifluorosilyl, and chlorodimethylsilyl; a stannyl group such as trimethyl stannyl and tributyl stannyl; a bornyl group such as dihydroxy bornyl; a compound having a substituent group such as a sulfonyl group such as triflate, nonaflate, a mesylate group, and a tosylate group, or a magnesium halide derivative or a zinc halide derivative which is activated with magnesium or zinc by using aryl halide as a raw material. At least one metal selected from copper, zinc, nickel, cobalt, palladium, zirconium, manganese, germanium, bismuth, lead, indium, and the like, or a compound thereof is preferably used as the metal catalyst coupling any two of the aryl compounds. Examples of the compound of the metal described above include a chloride, a bromide, an iodide, an acetate, an acetyl acetonate salt, a carbonate, a hydroxide, a nitrate, an organic complex, an activated carbon carrier, and the like.

In particular, among the reaction examples described above, a Suzuki coupling reaction (J. Organomet. Chem., 576, 147 (1999); Synth. Commun., 11, 513 (1981)) is preferable in which an aryl boronic acid reacts with an aryl halide or the like by using an organic palladium complex or the like as a catalyst in the coexistence of a base, from a viewpoint of easy availability of a reaction substrate or simple handleability, and ease of removing a byproduct. That is, the regioselective hetero coupling reaction of the method for producing the polyvalent hydroxy biphenyl having high purity in the present invention is a reaction in which at least one compound selected from aryl boronic acids, an anhydride thereof, and ester and a borate salt represented by Formula (2) described below reacts with aryl halide or aryl sulfonate represented by Formula (3) described below by using an organic palladium complex or the like as a catalyst in the coexistence of a base.

[Chem. 8]

(2)

[Chem. 9]

(3)

In Formula (2) or (3) described above, k1 and l1 each represent an integer of 0 to 4, m and n each represent an integer of 1 to 5, $R^1$ and $R^2$ each independently represent a hydrocarbon group having 1 to 10 carbon atoms which may have a substituent group, $R^1$ and $R^2$ may be identical to each other or different from each other, $R^3$ and $R^4$ each independently represent a hydrogen atom, a methyl group, a benzyl group, a tetrahydropyranyl group, a tetrahydrofuryl group, a methoxymethyl group, an ethoxymethyl group, or a silyl group such as a trimethyl silyl group, a tert-butyl dimethyl silyl group, and a triisopropyl silyl group, and X represents a chlorine atom, a bromine atom, an iodine atom, triflate, mesylate, tosylate, or nosylate.

Examples of the hydrocarbon group having 1 to 10 carbon atoms described above include an alkyl group such as a methyl group, an ethyl group, an isopropyl group, and a cyclohexyl group; an alkenyl group such as a vinyl group, an allyl group, and a cyclopropenyl group; an alkynyl group such as an ethynyl group and a propynyl group; an aryl group such as a phenyl group, a tolyl group, a xylyl group, and a naphthyl group; and an aralkyl group such as a benzyl group, a phenethyl group, and a naphthyl methyl group. The substituent group described above may include any substituent group insofar as the substituent group does not considerably affect the production step of the present invention. In consideration of a decrease in a melt viscosity of the epoxy resin which is produced by the production step of the present invention and an increase in crosslinking density of the cured product of the epoxy resin, the substituent group is a hydrogen atom or a hydrocarbon group having 1 to 4 carbon atoms, and is more preferably a hydrogen atom, a methyl group, or an allyl group.

Examples of $R^3$ and $R^4$ include a hydrogen atom, a methyl group, a benzyl group, a tetrahydropyranyl group, a tetrahydrofuryl group, a methoxymethyl group, an ethoxymethyl group, a silyl group such as a trimethyl silyl group, a tert-butyl dimethyl silyl group, and a triisopropyl silyl group, and the like. From a viewpoint of industrial availability at a low cost, a hydrogen atom or a methyl group is preferable as $R^3$ and $R^4$.

The aryl boronic acids represented by Formula (2) described above may have a structure of an anhydride, boronic acid ester, a borate salt, or the like which is dehydrated and trimerized. Examples of the boronic acid ester described above include alkyl ester such as —B(OMe)2 and B(OiPr)2; cyclic ester in which catechol or pinacol is condensed, and the like. In addition, examples of the borate salt include a trifluoroborate salt, a trihydroxy borate salt, an organic cyclic triol borate salt having bicyclo[2,2,2] octane, and the like.

X in Formula (3) described above represents a chlorine atom, a bromine atom, an iodine atom, triflate, mesylate, tosylate, or nosylate. From a viewpoint of easy availability and excellent reactivity of the raw material, a bromine atom or an iodine atom is preferable as X.

k1 and l1 in Formula (2) and Formula (3) described above represent an integer of 0 to 4, and m and n represent an integer of 1 to 5. As the sum of m and n becomes larger, the epoxy resin produced by the production method of the present invention is multifunctionalized and heat resistance is improved, but brittleness and moisture resistance deteriorate. Therefore, the sum of m and n is preferably 2 to 8, and is more preferably 3 to 6.

A molar ratio of the aryl boronic acids represented by Formula (2) described above and the aryl halide or the aryl sulfonate represented by Formula (3) described above is not particularly limited, and the molar ratio is preferably 1:1 to 5:1, and is more preferably 1:1 to 2:1 from a viewpoint of an excellent yield.

Examples of the metal catalyst used in the coupling reaction between the aryl boronic acids represented by Formula (2) described above and the aryl halide or the like represented by Formula (3) described above include palladium-activated carbon, a zerovalent palladium compound such as tetrakis(triphenyl phosphine) palladium (0), bis(dibenzylidene acetone) palladium (0), and tris(dibenzylidene acetone) dipalladium (0), and a divalent palladium compound such as palladium acetate (II), palladium chloride (II), bis(triphenyl phosphine) palladium (II) dichloride, [1,1'-bis(diphenyl phosphino) ferrocene] palladium (II) dichloride, [1,4-bis(diphenyl phosphino) butane] palladium (II) dichloride, bis(acetonitrile) palladium (II) dichloride, bis(benzonitrile) palladium (II) dichloride, an allyl palladium (II) chloride dimer, cyclopentadienyl allyl palladium (II), and palladium hydroxide. In addition, a nickel compound such as bis(triphenyl phosphine) nickel chloride and tetrakis(triphenyl phosphine) nickel, and the like are included in addition to the palladium compound. In addition, as necessary, two or more types of these compounds are able to be used. Furthermore, the palladium compound may be dissolved during the reaction or may be supported on any carrier. Among them, a palladium complex having tertiary phosphine as a ligand is preferable from a viewpoint of an excellent yield, and a palladium complex having triphenyl phosphine as a ligand is more preferable from a viewpoint of easy availability and an excellent yield. The used amount of a palladium catalyst is generally 0.00001 mol to 0.1 mol, and is preferably 0.001 mol to 0.05 mol, with respect to 1 mol of the aryl halide or the aryl sulfonate.

In addition, the coupling reaction between the aryl boronic acids represented by Formula (2) described above and the aryl halide or the like represented by Formula (3) described above is able to be performed in the existence of phosphines or imines. Among them, it is preferable that the coupling reaction is performed in the existence of triaryl phosphines, and it is more preferable that the coupling reaction is performed in the existence of triphenyl phosphine. When the phosphines or the imines are used, the used amount thereof is generally 0.5 mol to 5.0 mol, and is preferably 1.0 mol to 2.2 mol, with respect to 1 mol of the palladium compound.

It is essential that the coupling reaction between the aryl boronic acids represented by Formula (2) described above and the aryl halide or the like represented by Formula (3) described above is performed in the existence of a base. Examples of usable bases are able to include an alkali metal hydroxide such as lithium oxide, sodium hydroxide, and potassium hydroxide; an alkali earth metal hydroxide such as magnesium hydroxide and calcium hydroxide; an alkali metal carbonate such as sodium carbonate, potassium carbonate, and cesium carbonate; an alkali metal bicarbonate such as a sodium hydrogen carbonate and a potassium hydrogen carbonate; an alkali metal acetate such as sodium acetate and potassium acetate; an inorganic base such as an alkali metal phosphate such as sodium phosphate; metal hydrides such as sodium hydride and potassium hydride; alcohol metal salts such as sodium methoxide, sodium ethoxide, and potassium tert-butoxide; and an organic base such as triethyl amine, N,N-dimethyl aniline, pyridine, 4-N,N-dimethyl aminopyridine, and 1,8-diazabicyclo[5.4.0]-7-undecene, and these bases are able to be independently used or two or more types thereof are able to be used in combination, as necessary. Among them, the alkali metal carbonate is preferable from a viewpoint of an excellent yield. The used amount of the base is 0.5 mol to 5.0 mol, and is preferably 1.0 mol to 2.0 mol, with respect to 1 mol of the aryl halide or the aryl sulfonate.

The coupling reaction between the aryl boronic acids represented by Formula (2) described above and the aryl halide or the like represented by Formula (3) described above is generally performed by using a solvent. Examples of the solvent to be used include ethers such as diethyl ether, tetrahydrofuran (THF), and dioxane; aromatic hydrocarbons such as benzene, toluene, xylene, or chlorobenzene; an aprotic polar solvent such as N,N-dimethyl formamide (DMF), N,N-dimethyl acetamide, N-methyl-2-pyrrolidone, dimethyl sulfoxide, and sulfolane; nitriles such as acetonitrile and propionitrile; esters such as ethyl acetate and ethyl propionate; aliphatic hydrocarbons such as pentane, hexane, cyclohexane, and heptane; alcohols such as methanol and ethanol; and water, and these solvents are able to be independently used or two or more types thereof are able to be used in combination, as necessary. The used amount of the solvent is generally 0.1 times by weight to 50 times by weight, and is preferably 0.5 times by weight to 20 times by weight, with respect to the aryl halide or the aryl sulfonate.

The coupling reaction between the aryl boronic acids represented by Formula (2) described above and the aryl halide or the like represented by Formula (3) described above is performed at 0° C. to 150° C. A reaction time is different according to a reaction temperature, a reaction substrate, a reaction amount, and the like, and is generally in a range of 10 minutes to 20 hours.

In the production step of the polyvalent hydroxy biphenyl having high purity in the present invention, when $R^3$ or $R^4$ in Formula (2) and Formula (3) described above represents groups other than the hydrogen atom, a protective group of the hydroxyl group is deprotected by a known and common method after the regioselective cross-coupling reaction.

The method for producing the biphenyl-skeleton-containing epoxy resin of the present invention includes a step in which the polyvalent hydroxy biphenyl having high purity synthesized by the regioselective coupling reaction of the phenol derivative reacts with epihalohydrin. Specifically, examples of the step described above include a method in which a reaction is performed at a temperature of 20° C. to 120° C. for 0.5 hours to 10 hours while adding the epihalohydrin at a ratio of 2 times to 10 times (in terms of mole) with respect to the number of moles of a phenolic hydroxyl group of a phenol compound and collectively or gradually adding a basic catalyst at a ratio of 0.9 times to 2.0 times (in terms of mole) with respect to the number of moles of the phenolic hydroxyl group. The basic catalyst may be used in a state of a solid or an aqueous solution thereof, and when the aqueous solution is used, a method may be used in which the aqueous solution is continuously added, and the water and the epihalohydrins are continuously distilled from a reaction mixture under reduced pressure or under normal pressure, and are further separated, and thus the water is removed and the epihalohydrin continuously returns into the reaction mixture.

Furthermore, when industrial production is performed, all of the epihalohydrins used in the preparation are new in an initial batch of epoxy resin production, but the epihalohydrins collected from a crude reaction product and new epihalohydrins corresponding to the eliminated epihalohydrins as consumed epihalohydrins in the reaction are able to be used together in subsequent batches, and this is economically preferable. At this time, the epihalohydrin to be used is not particularly limited, and examples of the epihalohydrin include epichlorohydrin, epibromohydrin, β-methyl epichlorohydrin, and the like. Among them, the epichlorohydrin is preferable from a viewpoint of easy industrial availability.

In addition, specifically, examples of the basic catalyst described above include an alkali earth metal hydroxide, an alkali metal carbonate, an alkali metal hydroxide, and the like. In particular, the alkali metal hydroxide is preferable from a viewpoint of being excellent for catalyst activation of an epoxy resin synthesis reaction, and examples of the alkali metal hydroxide include sodium hydroxide, potassium hydroxide, and the like. When the catalyst is used, these basic catalysts may be used in a state of an aqueous solution of approximately 10 mass % to 55 mass % or may be in a state of a solid. In addition, it is possible to increase a reaction speed in the synthesis of the epoxy resin by using an organic solvent together. Such an organic solvent is not particularly limited, and examples of the organic solvent include ketones such as acetone and methyl ethyl ketone, alcohols such as methanol, ethanol, 1-propyl alcohol, isopropyl alcohol, 1-butanol, secondary butanol, and tertiary butanol, cellosolves such as methyl cellosolve and ethyl cellosolve, ethers such as tetrahydrofuran, 1,4-dioxane, 1,3-dioxane, and diethoxy ethane, an aprotic polar solvent such as acetonitrile, dimethyl sulfoxide, and dimethyl formamide, and the like. These organic solvents may be each independently used, and two or more types thereof may be suitably used in combination in order to adjust the polarity.

A reactant of the epoxidation reaction described above is washed with water, and then unreacted epihalohydrin or the organic solvent used together are distilled by distillation under heating and reduced pressure. In addition, in order to decrease hydrolyzable halogen in the epoxy resin, the reaction is able to be further performed by dissolving the obtained epoxy resin again in an organic solvent such as toluene, methyl isobutyl ketone, and methyl ethyl ketone, and by adding an aqueous solution of an alkali metal hydroxide such as sodium hydroxide and potassium hydroxide. At this time, in order to increase the reaction speed, a phase transfer catalyst such as a quaternary ammonium salt or crown ether may be included. When the phase transfer catalyst is used, a ratio of the used amount thereof to 100 parts by mass of the epoxy resin to be used is preferably 0.1 parts by mass to 3.0 parts by mass. After the reaction, the generated salt is removed by being filtered or being washed with water, and a solvent such as toluene and methyl isobutyl ketone is distilled under heating and reduced pressure, and thus the biphenyl-skeleton-containing epoxy resin of the present invention as an object is able to be obtained.

Furthermore, in the method for producing the biphenyl-skeleton-containing epoxy resin of the present invention, the epihalohydrin may react with the polyvalent hydroxy biphenyl having high purity synthesized in the regioselective coupling reaction of the phenol derivative within a range not impairing the effect of the present invention by using other polyvalent phenols together.

Further, according to the production method of the present invention, the epihalohydrin reacts with 2,4,4'-trihydroxy biphenyl represented by Formula (6) which is obtained by the production step including the regioselective cross-coupling reaction, and thus a 2,4,4'-trihydroxy biphenyl type epoxy resin represented by Formula (4) described below is able to be produced.

[Chem. 10]

(6)

[Chem. 11]

(4)

(In the formula, k1 represents an integer of 0 to 4, l1 represents an integer of 0 to 3, $R^1$ and $R^2$ each independently represent a hydrocarbon group having 1 to 10 carbon atoms which may have a substituent group, and $R^1$ and $R^2$ may be identical to each other or different from each other.)

Specifically, examples of the method for producing the epoxy resin include a method, including:

(i) A step of performing a reaction by using an aryl boronic acid represented by Formula (7) and aryl halide or aryl sulfonate represented by Formula (8) by using an organic palladium complex or the like as a catalyst in the coexistence of a base;

(ii) A step of deprotecting a hydroxyl group when $R^3$ and $R^4$ of Formula (7) and Formula (8) are groups other than a hydrogen atom; and (iii) A step of producing a 2, 4, 4'-trihydroxy biphenyl type epoxy resin represented by Formula (4) described above by allowing epihalohydrin to react with 2, 4, 4'-trihydroxy biphenyl represented by Formula (6) described above which is obtained in the step of (i) or (ii) described above.

Here, in the step of producing the 2,4,4'-trihydroxy biphenyl derivative represented by Formula (6) described above, when the regioselective coupling reaction progressing by the substituent group-metal exchange between the substituent group and the metal catalyst is performed, the raw material and the coupling method are not limited thereto.

[Chem. 12]

(7)

[Chem. 13]

(8)

(k1 represents an integer of 0 to 4, l1 represents an integer of 0 to 3, $R^1$ and $R^2$ each independently represent a hydrocarbon group having 1 to 10 carbon atoms which may have a substituent group, $R^1$ and $R^2$ may be identical to each other or different from each other, $R^3$ and $R^4$ each independently represent a hydrogen atom, a methyl group, a benzyl group, a tetrahydropyranyl group, a tetrahydrofuryl group, a methoxymethyl group, an ethoxymethyl group, or a silyl group such as a trimethyl silyl group, a tert-butyl dimethyl silyl group, and a triisopropyl silyl group, and X represents a chlorine atom, a bromine atom, an iodine atom, triflate, mesylate, tosylate, or nosylate.)

Further, according to the production method of the present invention, the epihalohydrin reacts with 3,4',5-trihydroxy biphenyl represented by Formula (9) which is obtained by the production step including the regioselective cross-coupling reaction, and thus it is possible to produce a 3,4',5-trihydroxy biphenyl type epoxy resin represented by Formula (5) described below.

[Chem. 14]

(9)

[Chem. 15]

(5)

(In the formula, k1 represents an integer of 0 to 4, l1 represents an integer of 0 to 3, $R^1$ and $R^2$ each independently represent a hydrocarbon group having 1 to 10 carbon atoms which may have a substituent group, and $R^1$ and $R^2$ may be identical to each other or different from each other.)

Specifically, examples of the production method of the epoxy resin include a method, including:

(i) a step of performing a reaction by using the aryl boronic acid represented by Formula (7) and aryl halide or aryl sulfonate represented by Formula (10) by using an organic palladium complex or the like as a catalyst in the coexistence of a base;

(ii) a step of deprotecting a hydroxyl group when $R^3$ and $R^4$ of Formula (7) and Formula (10) are groups other than a hydrogen atom; and (iii) a step of producing a 3,4',5-trihydroxy biphenyl type epoxy resin represented by Formula (5) described above by allowing epihalohydrin to react with 3,4',5-trihydroxy biphenyl represented by Formula (9) described above which is obtained in the step of (i) or (ii) described above.

Here, in the step of producing the 3,4',5-trihydroxy biphenyl represented by Formula (9) described above, when the regioselective coupling reaction progressing by the substituent group-metal exchange between the substituent group and the metal catalyst is performed, the raw material and the coupling method are not limited thereto.

[Chem. 16]

(7)

-continued

[Chem. 17]

(10)

(k1 represents an integer of 0 to 4, l1 represents an integer of 0 to 3, $R^1$ and $R^2$ each independently represent a hydrocarbon group having 1 to 10 carbon atoms which may have a substituent group, $R^1$ and $R^2$ may be identical to each other or different from each other, $R^3$ and $R^4$ each independently represent a hydrogen atom, a methyl group, a benzyl group, a tetrahydropyranyl group, a tetrahydrofuryl group, a methoxymethyl group, an ethoxymethyl group, or a silyl group such as a trimethyl silyl group, a tert-butyl dimethyl silyl group, and a triisopropyl silyl group, and X represents a chlorine atom, a bromine atom, an iodine atom, triflate, mesylate, tosylate, or nosylate.)

A cured product of the 2,4,4'-trihydroxy biphenyl type epoxy resin and the 3,4',5-trihydroxy biphenyl type epoxy resin described above exhibits excellent heat resistance derived from a biphenyl skeleton, low thermal expandability, and extremely excellent thermal conductivity.

A multifunctional low molecular weight epoxy resin such as a naphthalene type tetrafunctional epoxy resin (HP-4700, manufactured by DIC Corporation, epoxy equivalent of 160 g/eq to 170 g/eq, a softening point of 85° C. to 95° C., a melt viscosity at 150° C. of 0.3 Pa·s to 0.6 Pa·s, and a weight average molecular weight of 648) is known as an existing epoxy resin exhibiting excellent heat resistance. The existing epoxy resin is able to prepare a cured product exhibiting extremely high heat resistance, but is a solid and has a high melt viscosity, and thus workability deteriorates, and the cured product is not able to be independently prepared without using a curing agent. In contrast, the 2,4,4'-trihydroxy biphenyl type epoxy resin and the 3,4',5-trihydroxy biphenyl type epoxy resin of the present invention are a liquid or a crystal having a low melting point, and has a low melt viscosity, and thus workability is excellent, and for example, the cured product described above is able to be independently prepared. In addition, the resin of the present invention is able to be more highly filled with silica compared to the existing resin, and thus it is possible to prepare a encapsulation material having low thermal expandability, and more excellent flame retardance and thermal conductivity.

In addition, most of the existing liquid epoxy resins are a bifunctional glycidyl ether type epoxy resin such as a bisphenol A type epoxy resin or an alicyclic epoxy resin, and thus a cured product thereof is not able to express high heat resistance. Among the existing liquid epoxy resins, a naphthalene type bifunctional epoxy resin having high heat resistance (HP-4032D, manufactured by DIC Corporation, epoxy equivalent of 136 g/eq to 148 g/eq, and viscosity of 50 Pa·s to 60 Pa·s) does not satisfy performance requirements in the recent advanced material fields. However, the 2,4,4'-trihydroxy biphenyl type epoxy resin of the present invention is able to prepare a liquid encapsulation material or a liquid adhesive agent having high heat resistance by independently using the resins or by using the resins in combination with another liquid epoxy resin, and is able to be developed to an application in which higher heat resistance is required.

EXAMPLES

The present invention will be described in detail with reference to examples and comparative examples. Furthermore, a melt viscosity at 150° C., a softening point, a melting point, a GPC spectrum, an NMR spectrum, and an MS spectrum were measured in the following conditions.

1) Melt Viscosity at 150° C.: Measured by using the following device on the basis of ASTM D4287.
Device Name: MODEL CV-1S, manufactured by Codex Corporation 2) Softening Point Measurement Method: Measured by a ball & ring (B&R) method using glycerin as a heat medium on the basis of JIS K7234.
Device Name: ASP-M2 Type, manufactured by Meitec Company, Ltd.
Temperature Rising Rate: 5/min 3) Melting point: Measured by using a thermogravimetry/differential thermal analyzer (TG/DTA6200, manufactured by Hitachi High-Tech Science Corporation).
Measurement Conditions
Measurement Temperature: Room temperature to 300° C.
Measurement Atmosphere: Nitrogen
Temperature Rising Rate: 10° C./min 4) GPC: Measurement conditions are as follows.
Measurement Device: "GPC-104", manufactured by Showa Denko K. K.,
Column: "KF-401HQ", manufactured by Showa Denko K. K.
+"KF-401HQ", manufactured by Showa Denko K. K.
+"KF-402HQ", manufactured by Showa Denko K. K.
+"KF-402HQ", manufactured by Showa Denko K. K.
Detector: RI (a differential refractometer)
Standard: (Used Polystyrene)
"Polystyrene Standard 400", manufactured by Waters.
Sample: Obtained by filtering 1.0 mass % of a tetrahydrofuran solution in terms of solid resin using a microfilter (50 µl).

5) NMR: NMR LA300, manufactured by JEOL Ltd.
Solvent: Acetone-d6

6) MS: Gas chromatograph time-of-flight mass spectrometer JMS-T100GC, manufactured by JEOL Ltd.
Ionization Mode: FD
Cathode Voltage: −10 kV
Emitter Current: 0 mA→40 mA [25.6 mA/min.]
Solvent: Tetrahydrofuran
Sample Concentration: 2%

Synthesis Example 1

Synthesis of 3,4',5-Methoxy Biphenyl

A solution in which 110 g of 1-bromo-3,5-dimethoxy benzene, 257 g of isopropyl alcohol (hereinafter, referred to as IPA), and 139 g of potassium carbonate were dissolved in 107 g of water in advance was put into a flask attached with a thermometer, a stirrer, and a reflux cooler while performing a nitrogen gas purge, and nitrogen substitution was performed in a reaction vessel while stirring the solution, and then 5.9 g of tetrakistriphenyl phosphine palladium (0) was added to the solution, and a solution in which 83 g of a 4-methoxy phenyl boronic acid was dissolved in 109 g of IPA in advance was dripped thereto. A reaction liquid was heated and refluxed for 3 hours, and then 500 mL of water was added to the reaction liquid, an IPA layer was separated, and a water layer was extracted by being moved to a separating funnel and by adding 500 mL of toluene. Each organic layer was washed with a saturated solution of sodium chloride. A solvent was distilled under vacuum, and then a precipitate was filtered by adding 500 mL of toluene, and the toluene was distilled under reduced pressure. 200 mL of methanol was added to the obtained crude product, a precipitate was filtered, the mixture was dried by using a vacuum drier at 50° C. for 5 hours, and thus 113 g of 3,4',5-trimethoxy biphenyl was obtained.

Synthesis Example 2

Synthesis of 3,4',5-Trihydroxy Biphenyl 100 g of the 3,4',5-trimethoxy biphenyl obtained in Synthesis Example 1, 488 g of sodium iodide, and 628 g of acetonitrile were put into a flask attached with a thermometer, a stirrer, and a reflux cooler while performing a nitrogen gas purge, and then 356 g of trimethyl silane chloride was dripped thereto, and a reaction was performed at 50° C. for 18 hours. A reaction liquid was cooled to room temperature, and 500 mL of water was added thereto. The acetonitrile was distilled under reduced pressure, 1 L of ethyl acetate was added thereto, a mixed liquid was moved to a separating funnel, and an organic layer was separated, and then a water layer was extracted by the ethyl acetate. The combined organic layer was washed with an aqueous solution of saturated sodium hydrogen carbonate and a saturated solution of sodium chloride. An ethyl acetate solution was concentrated to approximately 200 mL under reduced pressure, and a crystal having the precipitated 3,4',5-trihydroxy biphenyl as a main component was filtered. 50 mL of ethyl acetate and 150 mL of toluene were added to the obtained residue and were heated and stirred at 80° C. for 10 minutes, an undissolved precipitate was filtered, the mixture was dried by using a vacuum drier at 50° C. for 5 hours, and thus 62 g of 3,4',5-trihydroxy biphenyl was obtained.

Synthesis Example 3

Synthesis of 2,4,4'-Trimethoxy Biphenyl

A solution in which 110 g of 1-bromo-2,4-dimethoxy benzene, 257 g of IPA, and 139 g of potassium carbonate were dissolved in 107 g of water in advance was put into a flask attached with a thermometer, a stirrer, and a reflux cooler while performing a nitrogen gas purge, and nitrogen substitution was performed in a reaction vessel while stirring the solution, and then 5.9 g of tetrakistriphenyl phosphine palladium (0) was added to the solution, and a solution in which 83 g of a 4-methoxy phenyl boronic acid was dissolved in 109 g of IPA in advance was dripped thereto. A reaction liquid was heated and refluxed for 3 hours, and then 500 mL of water was added to the reaction liquid, an IPA layer was separated, and a water layer was extracted by being moved to a separating funnel and by adding 500 mL of toluene. Each organic layer was washed with a saturated solution of sodium chloride. A solvent was distilled under vacuum, and then a precipitate was filtered by adding 500 mL of toluene, and the toluene was distilled under reduced pressure. 200 mL of methanol was added to the obtained crude product, a precipitate was filtered, the mixture was dried by using a vacuum drier at 50° C. for 5 hours, and thus 105 g of 2,4,4'-trimethoxy biphenyl was obtained.

Synthesis Example 4

Synthesis of 2,4,4'-Trihydroxy Biphenyl 100 g of the 2,4,4'-trimethoxy biphenyl obtained in Synthesis Example 3, 488 g of sodium iodide, and 628 g of acetonitrile were put into a flask attached with a thermometer, a stirrer, and a reflux cooler while performing a nitrogen gas purge, and then 356 g of trimethyl silane chloride was dripped thereto, and a reaction was performed at 60° C. for 8 hours. A reaction liquid was cooled to room temperature, and 500 mL of water was added thereto. The acetonitrile was distilled under reduced pressure, 1 L of ethyl acetate was added thereto, a mixed liquid was moved to a separating funnel, and an organic layer was separated, and then a water layer was extracted by the ethyl acetate. The combined organic layer was washed with an aqueous solution of saturated sodium hydrogen carbonate and a saturated solution of sodium chloride. An ethyl acetate solution was concentrated to approximately 200 mL under reduced pressure, and a crystal having the precipitated 2,4,4'-trihydroxy biphenyl as a main component was filtered. 50 mL of ethyl acetate and 150 mL of toluene were added to the obtained residue and were heated and stirred at 80° C. for 10 minutes, an undissolved precipitate was filtered, the mixture was dried by using a vacuum drier at 50° C. for 5 hours, and thus 52 g of 2,4,4'-trihydroxy biphenyl was obtained.

Example 1

Figure 1:
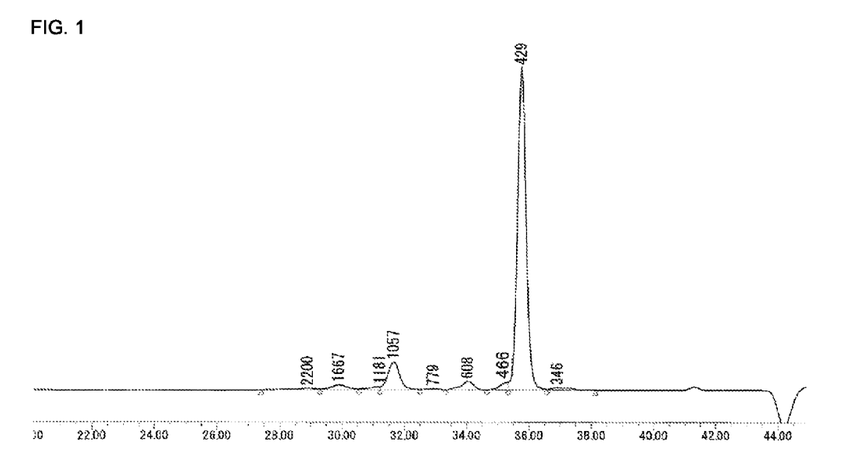
FIG. 1 is a GPC chart of 3,4',5-triglycidyloxy biphenyl obtained in Example 1.
Figure 2:
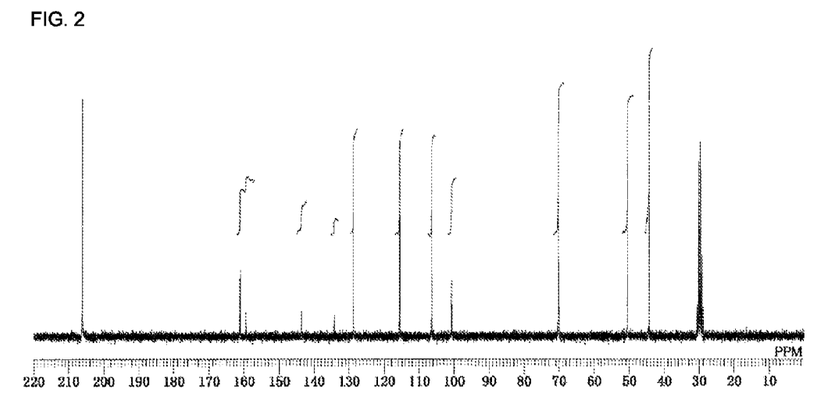
FIG. 2 is a C13NMR chart of 3,4',5-triglycidyloxy biphenyl obtained in Example 1.
Figure 3:
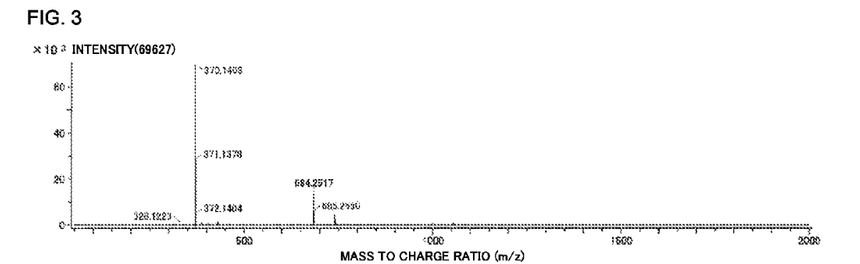
FIG. 3 is an MS chart of 3,4',5-triglycidyloxy biphenyl obtained in Example 1.

Synthesis of 3,4',5-Trihydroxy Biphenyl Type Epoxy Resin 43 g of 3,4',5-trihydroxy biphenyl obtained in Synthesis Example 2, 295 g of epichlorohydrin, and 103 g of n-butanol were put into a flask attached with a thermometer, a dripping funnel, a condenser, and a stirrer and were dissolved while performing a nitrogen gas purge. The temperature was increased to 40° C., and then 53 g of an aqueous solution of sodium hydroxide of 48 mass % was added to the mixture for 8 hours, and after that, the temperature was further increased to 50° C., and a reaction was further performed for 1 hour. After the reaction, 83 g of water was added thereto, the mixture was left to stand, and then the lower layer was removed. After that, unreacted epichlorohydrin was distilled at 150° C. under reduced pressure. 118 g of methyl isobutyl ketone was added and dissolved in the obtained crude epoxy resin. Further, 67 g of an aqueous solution of sodium hydroxide of 10 mass % was added to this solution, a reaction was performed at 80° C. for 2 hours, and then washing was repeatedly performed three times with water until the pH of a washing liquid became neutral. Next, the system was dehydrated due to azeotropy, a solvent was distilled under reduced pressure after passing through a precision filter, and thus 62 g of 3,4',5-triglycidyloxy biphenyl (A-1) which was a target epoxy resin was obtained. The obtained epoxy resin (A-1) was a crystal having a melting point of 97° C. in an ordinary temperature, and had a melt viscosity (a measurement method: ICI viscosimeter method, and a measurement temperature: 150° C.) of 0.27 dPa·s and epoxy equivalent of 135 g/eq. A GPC chart of the obtained epoxy resin is illustrated in FIG. 1, a C13NMR chart is illustrated in FIG. 2, and an MS spectrum is illustrated in FIG. 3. A peak of 370 indicating the 3,4',5-triglycidyloxy biphenyl (A-1) was detected from the MS spectrum. Furthermore, in the GPC chart of FIG. 1, a measured molecular weight obtained from a calibration curve was shifted from the actual molecular weight, and thus the molecular weight of each peak was corrected on the basis of the MS spectrum.

Example 2

Figure 4:
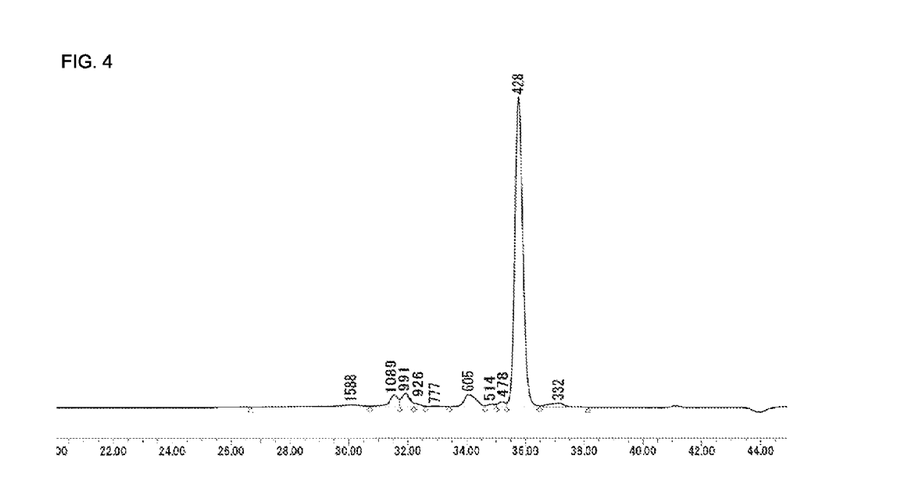
FIG. 4 is a GPC chart of 2,4,4'-triglycidyloxy biphenyl obtained in Example 2.
Figure 5:
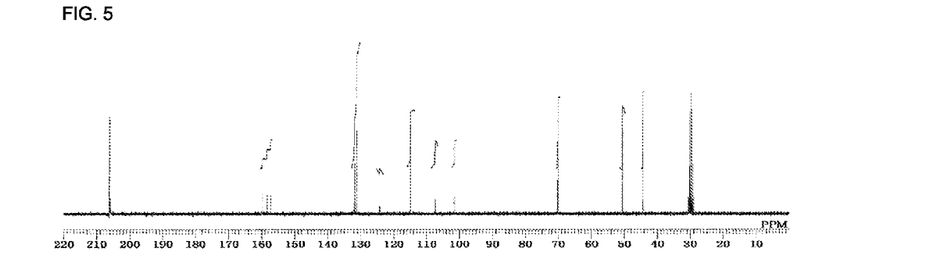
FIG. 5 is a C13NMR chart of 2,4,4'-triglycidyloxy biphenyl obtained in Example 2.
Figure 6:
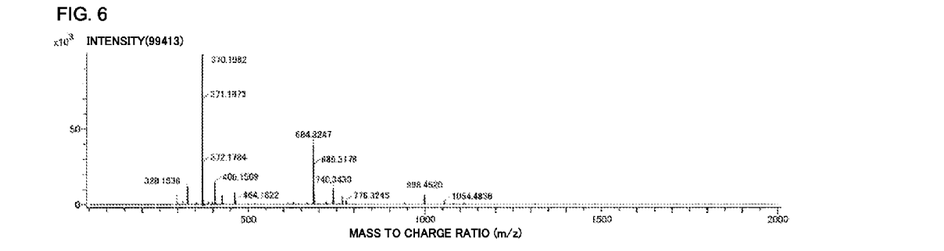
FIG. 6 is an MS chart of 2,4,4'-triglycidyloxy biphenyl obtained in Example 2.

Synthesis of 2,4,4'-Trihydroxy Biphenyl Type Epoxy Resin 43 g of the 2,4,4'-trihydroxy biphenyl obtained in Synthesis Example 4, 295 g of epichlorohydrin, and 103 g of n-butanol were put into a flask attached with a thermometer, a dripping funnel, a condenser, and a stirrer and were dissolved while performing a nitrogen gas purge. The temperature was increased to 40° C., and then 53 g of an aqueous solution of sodium hydroxide of 48 mass % was added to the mixture for 8 hours, and after that, the temperature was further increased to 50° C., and a reaction was further performed for 1 hour. After the reaction, 83 g of water was added thereto, the mixture was left to stand, and then the lower layer was removed. After that, unreacted epichlorohydrin was distilled at 150° C. under reduced pressure. 118 g of methyl isobutyl ketone was added and dissolved in the obtained crude epoxy resin. Further, 67 g of an aqueous solution of sodium hydroxide of 10 mass % was added to this solution, a reaction was performed at 80° C. for 2 hours, and then washing was repeatedly performed three times with water until the pH of a washing liquid became neutral. Next, the system was dehydrated due to azeotropy, a solvent was distilled under reduced pressure after passing through a precision filter, and thus 63 g of 2,4,4'-triglycidyloxy biphenyl (A-2) which was a target epoxy resin was obtained. The obtained epoxy resin (A-2) was in a liquid state having viscosity of 943 Pa·s in an ordinary temperature, and had a melt viscosity (a measurement method: ICI viscosimeter method, and a measurement temperature: 150° C.) of 0.14 dPa·s and epoxy equivalent of 133 g/eq. A GPC chart of the obtained epoxy resin is illustrated in FIG. 4, a C13NMR chart is illustrated in FIG. 5, and an MS spectrum is illustrated in FIG. 6. A peak of 370 indicating the 2,4,4'-triglycidyloxy biphenyl (A-2) was detected from the MS spectrum. Furthermore, in the GPC chart of FIG. 4, a measured molecular weight obtained from a calibration curve was shifted from the actual molecular weight, and thus the molecular weight of each peak was corrected on the basis of the MS spectrum.

Examples 3 to 8 and Comparative Examples 1 to 5

The epoxy resins (A-1 and A-2) of the present invention obtained in Examples 1 and 2, and a 3,3',5,5'-tetramethyl-4,4'-biphenol type epoxy resin (A-3), a naphthalene type tetrafunctional epoxy resin HP-4700 (manufactured by DIC Corporation)(A-4) and a naphthalene type bifunctional epoxy resin HP-4032D (manufactured by DIC Corporation) (A-5) as a comparative epoxy resin, a phenol novolak type phenol resin TD-2131 (manufactured by DIC Corporation, hydroxyl group equivalent of 104 g/eq) and a methyl himic anhydride MHAC-P (manufactured by Hitachi Chemical Co., Ltd., neutralization equivalent of 89 g/eq) as a curing agent, and triphenyl phosphine (TPP) and imidazole (2P4MHZ-PW and 2E4MZ (both are manufactured by Shikoku Chemicals Corporation.)) as a curing accelerator were blended with each other as the composition shown in Table 1, and heat resistance, coefficient of linear thermal expansion, and thermal conductivity of a cured product which was prepared according to any one of the following curing conditions (I) to (III) were evaluated. Properties of each of the epoxy resins and properties of the cured products thereof are shown in Table 1.

<Curing Conditions (I)>
A blended product was poured into a mold form of 11 cm×9 cm×2.4 mm and was molded by a press at a temperature of 150° C. for 10 minutes, and then a molded product was taken out from the mold form, and subsequently, the molded product was cured at a temperature of 175° C. for 5 hours.

<Curing Conditions (II)>
A blended product was poured into a mold form of 6 cm×11 cm×0.8 mm and was temporarily cured at a temperature of 130° C. for 2 hours, and then a molded product was taken out from the mold form, and subsequently, the molded product was cured at a temperature of 170° C. for 2 hours and at a temperature of 250° C. for 8 hours.

<Curing Conditions (III)>
A blended product was poured into a mold form of 6 cm×11 cm×0.8 mm and was temporarily cured at a temperature of 110° C. for 2 hours, and a molded product was taken out from the mold form, and subsequently, the molded product was cured at a temperature of 250° C. for 2 hours.

<Heat Resistance (Glass Transition Temperature; Tg(DMA)>
A temperature at which a change in elastic modulus was maximized (a tan δ change rate was maximized) was evaluated as a glass transition temperature by using a viscoelasticity measurement device (DMA: a solid viscoelasticity measurement device RSAII, manufactured by Rheometric Scientific Inc., a rectangular tension method; a frequency of 1 Hz and a temperature rising rate of 3° C./min).

<Heat Resistance (Thermal Decomposition Temperature at 5% Weight Loss)>
A thermal decomposition temperature at 5% weight loss was measured by using a thermogravimetry/differential thermal analyzer (TG/DTA6200, manufactured by Hitachi High-Tech Science Corporation).
Measurement Conditions
Measurement Temperature: Room temperature to 500° C.
Measurement Atmosphere: Nitrogen
Temperature Rising Rate: 10° C./min <Linear Expansion Coefficient>
Thermomechanical analysis was performed in a tensile mode by using a thermomechanical analyzer (TMA: TMA-50, manufactured by Shimadzu Corporation).
Measurement Conditions
Load: 1.5 g
Temperature Rising Rate: 2 times at 10° C./min
Measurement Temperature Range: 50° C. to 300° C.
The measurement in the conditions described above was performed with respect to the same sample two times, and in the second measurement, an average expansion coefficient was evaluated as a coefficient of linear thermal expansion in a temperature range of 25° C. to 280° C.

<Thermal Conductivity>
A coefficient of thermal conductivity (λ) was calculated on the basis of an expression of $\lambda = \alpha \rho C$ by using a density ($\rho$), a coefficient of thermal diffusivity ($\alpha$), and a specific heat capacity (C). A specific weight, the coefficient of thermal diffusivity, and specific heat capacity were respectively obtained by the following method.

(1) Specific Gravity

The specific gravity was measured by using an electronic balance CP224S and a specific gravity measurement kit YDK01CP (manufactured by Sartorius AG).

(2) Coefficient of Thermal Diffusivity

The coefficient of thermal diffusivity at 25° C. was measured by using a coefficient of thermal diffusivity measurement device LFA447 Nanoflash (manufactured by NETZSCH-Geratebau GmbH).

(3) Specific Heat Capacity

The specific heat capacity at 25° C. was calculated by using a differential scanning calorimeter EXSTAR7200 (manufactured by Hitachi High-Tech Science Corporation).

Measurement Conditions
Measurement Temperature: −20° C. to 100° C.
Measurement Atmosphere: Nitrogen
Temperature Rising Rate: 10° C./min

The invention claimed is:

1. A method for producing a biphenyl-skeleton-containing epoxy resin represented by Formula (1) described below, comprising:
a step of allowing a polyvalent hydroxy biphenyl obtained by a production step including a regioselective cross-coupling reaction to react with epihalohydrin:

(1)

TABLE 1

| | | Example 3 | Example 4 | Example 5 | Example 6 | Example 7 | Example 8 | Comparative Example 1 | Comparative Example 2 | Comparative Example 3 | Comparative Example 4 |
|---|---|---|---|---|---|---|---|---|---|---|---|
| Epoxy Resin (Parts by Weight) | A-1 | 45 | 38 | 80 | | | | | | | |
| | A-2 | | | | 44 | 38 | 80 | | | | |
| | A-3 | | | | | | | 52 | 80 | | |
| | A-4 | | | | | | | | | 80 | |
| | A-5 | | | | | | | | | | 80 |
| | Properties | Solid | Solid | Solid | Liquid | Liquid | Liquid | Solid | Solid | Solid | Liquid |
| | Viscosity (Pa · s) | | | | 943 | 943 | 943 | | | | 23 |
| | Softening Point (° C.) | 97 (Melting Point) | 97 (Melting Point) | 97 (Melting Point) | | | | 105 (Melting Point) | 105 (Melting Point) | 91 | |
| | Melt Viscosity at 150° C. (dPa · s) | 0.27 | 0.27 | 0.27 | 0.14 | 0.14 | 0.14 | 0.18 | 0.18 | 4.5 | 0.07 |
| Curing Agent (Parts by Weight) | TD-2131 | 35 | | | 36 | | | 28 | | | |
| | MHAC-P | | 42 | | | 42 | | | | | |
| Catalyst (Parts by Weight) | TPP | 0.8 | | | 0.8 | | | 0.8 | | | |
| | 2P4MHZ-PW | | 0.4 | | | 0.4 | | | | | |
| | 2E4MZ | | | 1.6 | | | 1.6 | | 1.6 | 1.6 | 1.6 |
| Physical Properties of Cured Product | Tg(DMA) | 205 | 305 | Less | 199 | 295 | Less | 150 | 193 | — | 217 |
| | thermal decomposition temperature at 5% weight loss (° C.) | 400 | 369 | 396 | 398 | 367 | 395 | 353 | 365 | — | 388 |
| | coefficient of linear thermal expansion (ppm) | 120 | 74 | 84 | 124 | 77 | 87 | 151 | 118 | — | 91 |
| | Thermal Conductivity (W/m · K) | | | 0.31 | | | 0.32 | | 0.25 | — | 0.25 |
| | Curing Conditions | (I) | (II) | (III) | (I) | (II) | (III) | (I) | (III) | (III) | (III) |
| | Result | | | | | | | | | Gellation Occurs during Preparation of Composition | |

INDUSTRIAL APPLICABILITY

An epoxy resin in which polyvalent hydroxy biphenyl obtained by a production step including a regioselective cross-coupling reaction of a phenol derivative is glycidylated has liquid properties or a low melt viscosity, and a cured product thereof exhibits excellent performance in heat resistance, low thermal expandability, and thermal conductivity.

in the formula, k1 and l1 each represent an integer of 0 to 4, m and n each represent an integer of 1 to 5, $R^1$ and $R^2$ each independently represent a hydrocarbon group having 1 to 10 carbon atoms which may have a substituent group, and $R^1$ and $R^2$ may be identical to each other or different from each other, provided that left and right phenyl structures of a biphenyl skeleton are different from each other.

2. The method for producing a biphenyl-skeleton-containing epoxy resin according to claim 1, wherein the regioselective cross-coupling reaction is a cross-coupling reaction between at least one compound selected from aryl boronic acids and an anhydride thereof, ester and a borate salt represented by Formula (2) described below, and at least one compound selected from aryl halide or aryl sulfonate represented by Formula (3) described below:

(2)

(3)

k1 and l1 each represent an integer of 0 to 4, m and n each represent an integer of 1 to 5, $R^1$ and $R^2$ each independently represents a hydrocarbon group having 1 to 10 carbon atoms which may have a substituent group, $R^1$ and $R^2$ may be identical to each other or different from each other, $R^3$ and $R^4$ each independently represent a hydrogen atom, a methyl group, a benzyl group, a tetrahydropyranyl group, a tetrahydrofuryl group, a methoxymethyl group, an ethoxymethyl group, a silyl group, a trimethyl silyl group, a tert-butyl dimethyl silyl group, or a triisopropyl silyl group, and X represents a chlorine atom, a bromine atom, an iodine atom, triflate, mesylate, tosylate, or nosylate.

* * * * *